United States Patent
Tavakoli et al.

(10) Patent No.: US 9,386,960 B2
(45) Date of Patent: Jul. 12, 2016

(54) MULTIMODAL CARDIAC PHANTOM FOR IMAGING

(71) Applicant: University of Louisville Research Foundation, Inc., Louisville, KY (US)

(72) Inventors: Vahid Tavakoli, Louisville, KY (US); Amir A. Amini, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 182 days.

(21) Appl. No.: 14/021,756

(22) Filed: Sep. 9, 2013

(65) Prior Publication Data

US 2014/0069215 A1     Mar. 13, 2014

Related U.S. Application Data

(60) Provisional application No. 61/874,454, filed on Sep. 6, 2013, provisional application No. 61/698,368, filed on Sep. 7, 2012.

(51) Int. Cl.
| | |
|---|---|
| G09B 23/28 | (2006.01) |
| A61B 6/00 | (2006.01) |
| A61B 5/055 | (2006.01) |
| A61B 8/00 | (2006.01) |
| G01R 33/58 | (2006.01) |
| A61B 5/00 | (2006.01) |

(52) U.S. Cl.
CPC ............ *A61B 6/583* (2013.01); *A61B 5/055* (2013.01); *A61B 8/587* (2013.01); *G01R 33/58* (2013.01); *A61B 5/0044* (2013.01); *A61B 5/7285* (2013.01)

(58) Field of Classification Search
USPC ............. 434/262, 267, 268, 272, 273, 274
See application file for complete search history.

(56) References Cited

U.S. PATENT DOCUMENTS

| | | | | |
|---|---|---|---|---|
| 5,052,934 | A * | 10/1991 | Carey et al. ................. | 434/268 |
| 5,634,797 | A * | 6/1997 | Montgomery ............... | 434/268 |
| 6,474,993 | B1 * | 11/2002 | Grund et al. ................ | 434/262 |
| 7,083,418 | B2 * | 8/2006 | Baldauf ....................... | 434/272 |
| 7,255,565 | B2 * | 8/2007 | Keegan ........................ | 434/272 |
| 7,549,866 | B2 * | 6/2009 | Cohen et al. ................ | 434/267 |
| 7,798,815 | B2 * | 9/2010 | Ramphal et al. ............ | 434/265 |
| 8,480,407 | B2 * | 7/2013 | Campbell et al. ........... | 434/272 |
| 8,535,061 | B2 * | 9/2013 | Boutchko et al. ........... | 434/267 |
| 8,535,062 | B2 * | 9/2013 | Nguyen ....................... | 434/267 |
| 8,608,483 | B2 * | 12/2013 | Trotta et al. ................. | 434/267 |
| 8,678,830 | B2 * | 3/2014 | Gurdin et al. ............... | 434/265 |
| 8,708,707 | B2 * | 4/2014 | Hendrickson et al. ...... | 434/267 |
| 8,801,438 | B2 * | 8/2014 | Sakezles ..................... | 434/274 |
| 8,870,576 | B2 * | 10/2014 | Millon et al. ................ | 434/267 |
| 8,911,238 | B2 * | 12/2014 | Forsythe ..................... | 434/267 |
| 2007/0218437 | A1 * | 9/2007 | Lotano et al. ............... | 434/236 |
| 2008/0160259 | A1 * | 7/2008 | Nielson et al. .............. | 428/148 |
| 2009/0297441 | A1 * | 12/2009 | Canham et al. ............. | 424/1.61 |
| 2011/0291321 | A1 * | 12/2011 | Chan et al. .................. | 264/222 |
| 2014/0106329 | A1 * | 4/2014 | Watanabe et al. ........... | 434/272 |

* cited by examiner

*Primary Examiner* — Kurt Fernstrom
(74) *Attorney, Agent, or Firm* — Stites & Harbison, PLLC; Jeffrey A. Haeberlin; Terry L. Wright

(57) ABSTRACT

A multimodal cardiac phantom has a body structure with a shape and properties that mimic the elasticity, ultrasound, and magnetic properties of cardiac tissue. The multimodal cardiac phantom is advantageously produced from a polymer such as polyvinyl alcohol. The polyvinyl alcohol may include magnetic resonance imaging (MRI) markers and ultrasound markers. The multimodal cardiac phantom can be used to evaluate and to configure apparatuses for imagining cardiac tissue.

19 Claims, 15 Drawing Sheets
(8 of 15 Drawing Sheet(s) Filed in Color)

MULTIMODAL CARDIAC PHANTOM FOR IMAGING

CROSS-REFERENCE TO RELATED APPLICATIONS

This application claims the benefit of U.S. Provisional Application No. 61/698,368, filed on Sep. 7, 2012, and U.S. Provisional Application No. 61/874,454, filed on Sep. 6, 2013, both herein incorporated by reference.

FIELD OF THE INVENTION

The present invention relates to cardiac phantoms (i.e. physical models), apparatuses, and methods for evaluating and developing cardiac imaging devices and methods. In particular, the presently-disclosed subject matter relates to cardiac phantoms having a body structure and an upper portion that are each configured to mimic the elasticity, ultrasound, and magnetic properties of normal or diseased cardiac tissue.

BACKGROUND OF THE INVENTION

Heart disease is the leading cause of death in the modern world. The main contributor to the heart diseases is coronary occlusion, which subsequently leads to ischemic heart disease (IHD) and leads to myocardial compromise that presents itself as a decreased range of displacement of the myocardium and reduced thickening. As such, clinicians often make use of imaging techniques for the assessment of heart motion and the underlying myocardial perfusion. In this regard, the clinicians assess the myocardial motion subjectively by scoring the motion as normal, hypokinetic, akinetic, or dyskinetic. However, the conventional myocardial motility scoring is subjective and suffers from inter- and intra-observer variability [1].

Registration and motion estimation algorithms are significant areas of research in the medical imaging community with the goal of aiding the clinicians to achieve more objective outputs. Nevertheless, in vivo validation of registration techniques is not a trivial task since the ground truth motion field of the cardiac displacement is not known exactly. Older validation techniques such as sonomicrometry or implanted markers are invasive and limited to just one point of the cardiac tissue. Additionally, the surgical implantation of markers may change the local heart motion due to local damage. Comparison with the other modalities such as Tagged MR and TDI can be helpful. However, pixel to pixel intermodality comparison may need registration because the two images will not fully correspond. One approach to validation is a controlled experimental phantom setup that can simulate the anatomy and physiology of the heart. To date, however, a cardiac phantom has yet to be developed that is capable of mimicking the elasticity, ultrasound, and magnetic properties of both normal and diseased cardiac tissue.

SUMMARY OF THE INVENTION

The present invention relates to cardiac phantoms which have physical characteristics and properties that mimic the shape of a heart and, more specifically, cardiac tissue. The present cardiac phantoms are produced from a material which will appear as cardiac tissue when viewed using various cardiac imaging techniques including magnetic resonance imaging (MRI). In addition, the cardiac phantom can be produced to appear as diseased cardiac tissue when observed using various cardiac imaging devices. As a result, various cardiac phantoms in accordance with the present disclosure can be used to adjust and evaluate cardiac imaging devices.

The cardiac phantoms can be produced from a suitable material and will vary depending on the cardiac imaging apparatus and technique. One advantageous cardiac phantom material comprises polyvinyl alcohol (PVA) including polyvinyl alcohol cryogel (PVA-C). Further, the polyvinyl alcohol (base material) may include additional material such as ultrasound markers and MRI markers. For example, an ultrasound marker can be plastic microspheres made of silicon particles having an average diameter size of 1-2 mm. In some embodiments, dense PVA-C particles having an average diameter of 1-3 mm can be used as MRI markers.

The present cardiac phantoms are advantageously produced in a mold that has an interior surface that mimics the exterior surface of a heart. Further, the mold has an insert having an exterior surface that mimics the interior surfaces of a heart's left and right atriums and left and right ventricles. As a result, the mold can be used to produce a cardiac phantom by pouring liquefied or molten polymer into the mold with the mold insert in place inside the mold.

The present invention, in one form thereof, relates to a multimodal cardiac phantom. The phantom includes a body structure defining a first compartment and a second compartment. The first compartment and the second compartment each include a hollow upper chamber and a hollow lower chamber. The body structure has a shape to mimic the shape of a heart and comprises a material configured to mimic the elasticity, ultrasound, and magnetic properties of cardiac tissue. In one advantageous form, the body comprises cross-linking polyvinyl alcohol cryogel (PVA-C). In one further specific embodiment, dense PVA-C particles are included in the body which function as MRI markers. In one specific further embodiment, the PVA-C particles have an average diameter of 1-3 mm. In an alternative further embodiment, the body further comprises silicon microspheres which function as ultrasound markers.

Advantageously, the cardiac phantom may include an upper portion defining a connecting chamber for connecting the body structure to a connecting tube and for placing the first compartment and second compartment in fluid communication with each other and with the connecting chamber.

In yet an additional further embodiment, the multimodal cardiac phantom comprises a first valve separating the upper chamber of the first compartment from the lower chamber of the first compartment and a second valve separating the upper chamber of the second compartment from the lower chamber of the second compartment.

The present multimodal cardiac phantom can be used to evaluate cardiac imaging devices. The present cardiac phantom has physical and cardiac imaging properties that mimic a heart. If desired, the cardiac phantom can be modified in order to mimic diseased tissue. Stiffened polymeric material can be produced in the cardiac phantom to mimic diseased cardiac tissue. For example, a series of freeze-thaw cycles of the polymer of the cardiac phantom results in a reduction in elasticity of the resulting body structure. The resulting material, i.e. stiffened polymeric material, appears in cardiac imaging as diseased cardiac tissue.

The present invention in another form thereof relates to an apparatus for simulating cardiac structure and function. The apparatus includes a cardiac phantom having a body structure defining a first compartment and a second compartment. The first compartment and the second compartment each include a hollow upper chamber and a hollow lower chamber. The body structure has a shape to simulate a heart and is comprised of a material configured to mimic elasticity, ultrasound, and magnetic properties of cardiac tissue. The apparatus further includes a pump for transferring an amount of a fluid to the cardiac phantom and a connecting tube for connecting the cardiac phantom to the pump. A waveform generator is operably connected to the pump for controlling the timing and the amount of fluid delivered to the cardiac phantom. In some embodiments of the apparatus, the body structure includes an amount of a stiff PVA material having a shape and elasticity different than that of the material used for a remainder of the body structure such that the body structure is configured to mimic diseased cardiac tissue.

The present invention in another form thereof relates to a method for evaluating a cardiac imaging system. The method includes providing a cardiac phantom having a body structure defining a first compartment and a second compartment. The first compartment and second compartment each have a hollow upper chamber and a hollow lower chamber. The body structure has a shape to simulate a heart and is comprised of a material that mimics elasticity, ultrasound, and magnetic properties of cardiac tissue. The method further includes pouring an amount of fluid into the cardiac phantom and imaging the cardiac phantom as a liquid is being pumped.

The present invention, in another form thereof, relates to a method for manufacturing a multimodal cardiac phantom. The method comprises heating a polymer to a temperature to liquefy the polymer. The liquefied polymer is introduced into a mold having a mold insert. The mold has interior surfaces which mimic the exterior shape of a heart. The mold insert has an exterior surface and shape which mimics the interior surfaces of the left atrium and left ventricle chambers and the right atrium and right ventricle chambers of a heart. The liquefied polymer is cooled to harden the polymer to form the multimodal cardiac phantom. The cardiac phantom is removed from the mold wherein the cardiac phantom comprises left and right upper chambers and left and right lower chambers produced from the mold insert.

Further features and advantages of the present invention will become evident to those of ordinary skill in the art after a study of the description, figures, and non-limiting examples in this document.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DESCRIPTION OF EXEMPLARY EMBODIMENTS

Figure 1:
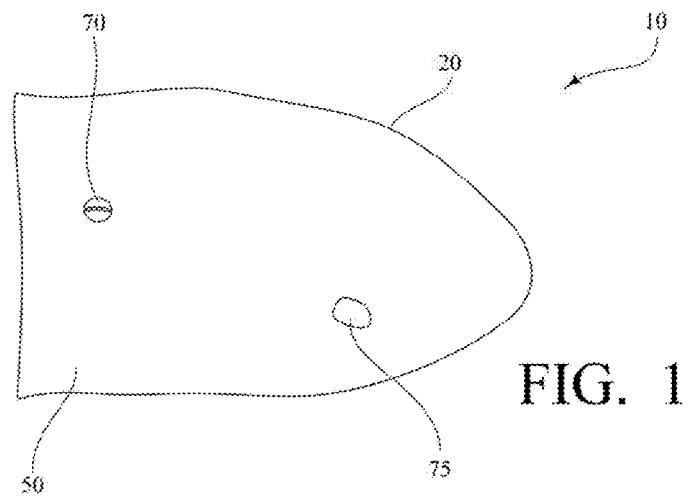
FIG. 1 is a plan side view of an exemplary cardiac phantom in accordance with the present invention.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by one of ordinary skill in the art, definitions are set forth herein to facilitate explanation of the presently-disclosed subject matter. Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

Dynamic cardiac phantoms, such as those of the present disclosure, can be used to evaluate and develop ultrasound and cardiac magnetic resonance (MR) motion tracking and registration methods. In this regard, in some embodiments of the present invention, a four chamber multimodal cardiac phantom has been designed and fabricated to simulate normal and pathologic hearts with different degrees of "infarction" and "scar tissues." In this set up, cardiac valves have been designed and fabricated as well. The four-chamber structure can simulate the asymmetric ventricular, atrial and valve motions, and can simulate the shape, elasticity, and magnetic resonance and ultrasound properties of the heart.

Figure 2:
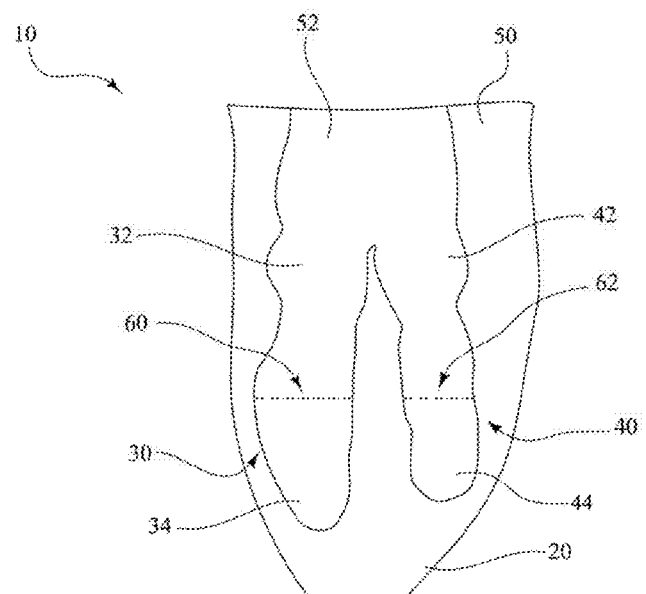
FIG. 2 is a sectional view of the cardiac phantom of FIG. 1.
Figure 3:
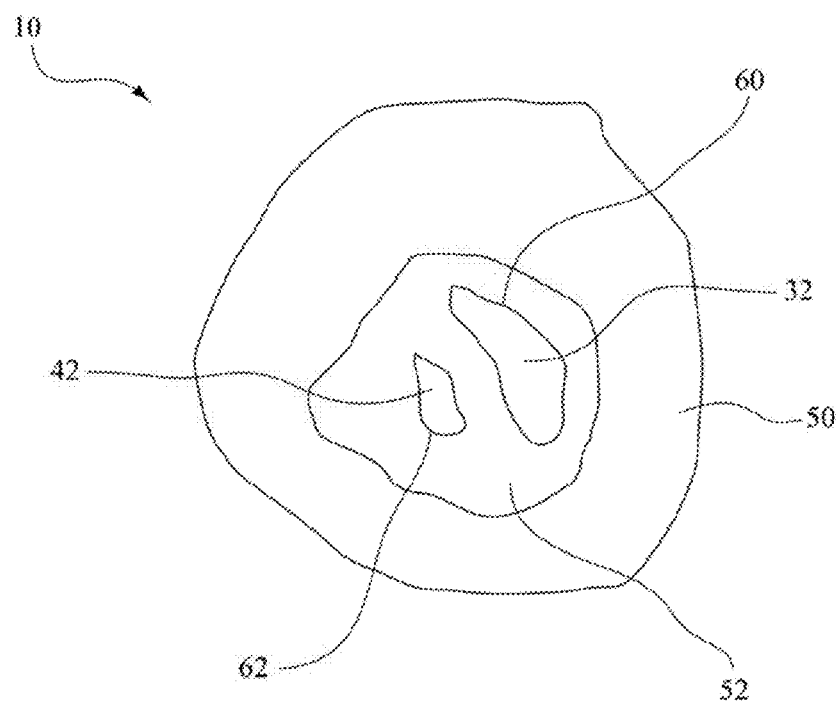
FIG. 3 is a top plan view of the cardiac phantom of FIG. 1.

The present multimodal cardiac phantom will now be described with regard to the present figures. Referring to FIGS. 1-3, an exemplary multimodal cardiac phantom 10 includes a body structure 20 and an upper portion 50. The body structure 20 and the upper portion 50 of the cardiac phantom 10 have a shape that is configured to simulate a heart, including both a functioning normal heart and a diseased heart.

The body structure 20 defines a right portion 30 and a left portion 40 corresponding to anatomical portions of a heart, namely the right atrium and right ventricle and the left atrium and left ventricle. The right portion 30 and left portion 40 each include a hollow upper chamber 32, 42, and a hollow lower chamber 34, 44, respectively. A bicuspid valve or flap 60 divides and partially separates hollow upper chamber 32 from lower chamber 34 and a tricuspid valve or flap 62 divides upper chamber 42 from lower chamber 44.

The upper portion 50 of the cardiac phantom 10 defines a connecting chamber 52 for connecting the body structure 20 to a connecting tube and for placing the first compartment 30 and the second compartment 40 in fluid communication with each other and with the connecting chamber 52.

The cardiac phantom 10 is comprised of a material configured to mimic the elasticity, ultrasound, and magnetic properties of a cardiac tissue. In some embodiments, the material used to produce the cardiac phantom 10 is polyvinyl alcohol (PVA) as PVA has been observed to be capable of mimicking the mechanical and acoustical properties of the heart. Although polyvinyl alcohol (PVA) is one advantageous material, other polymers can be used which produce a cardiac phantom having the requisite elasticity, mechanical and acoustical properties of a heart when observed using a desired cardiac imaging process. For example, other materials can be used and identified using routine experimentation by producing a cardiac phantom in accordance with this disclosure and testing the resulting cardiac phantom to determine that it is acceptable when observed using a desired cardiac imaging apparatus and technique.

In some embodiments of the present invention, the cardiac phantom 10 can include a stiffer polymeric material (i.e., a material having less elasticity than PVA) to thereby produce a cardiac phantom having mechanical properties that more closely resemble or mimic diseased cardiac tissue such as what is found in an infarcted heart. In some embodiments, the stiffened material (inclusions) has different shapes and different degrees of elasticity such that the stiffer inclusions are able to simulate abnormal cardiac segments or diseased tissue.

Referring still to FIGS. 1-3, the upper portion 50 further defines an outlet 75 (FIG. 1) for allowing fluid in the first compartment 30 to exit the hollow lower chamber 34 of the body structure 20. One or more holes 70 are further included in the upper portion 50 for securing the upper portion 50 to a connecting tube such that the cardiac phantom 10 can be used as part of an apparatus for simulating a cardiac structure and function.

The multimodal phantom 10 takes into consideration the shape of the heart as well as its biophysical and biomechanical parameters. Imaging properties such as the speed of the sound, ultrasound attenuation and T1/T2 of the heart should be considered. Simulation of the pathologies such as scarred myocardium and different stroke volumes are an advantage.

Figure 4:
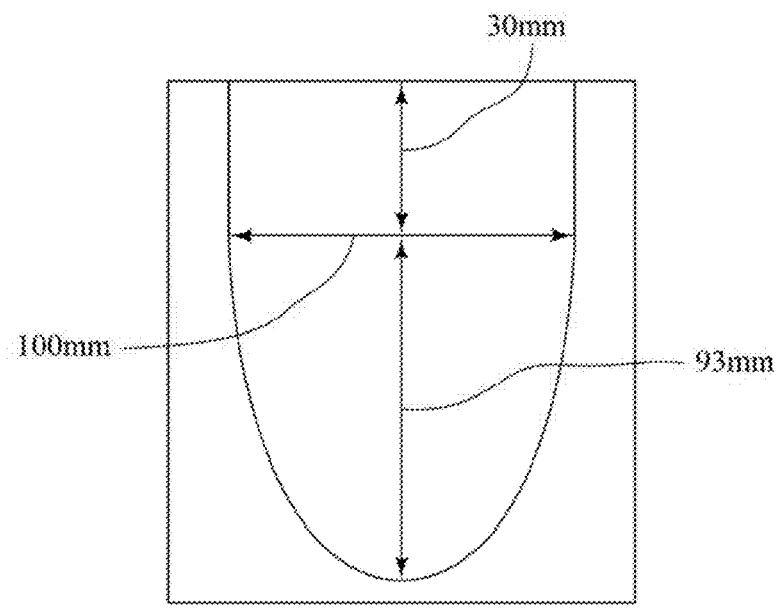
FIG. 4 shows the dimensions of a mold for creating a cardiac phantom of FIGS. 1-3, the numbers describing the widest diameter of each region in mm.
Figure 5:
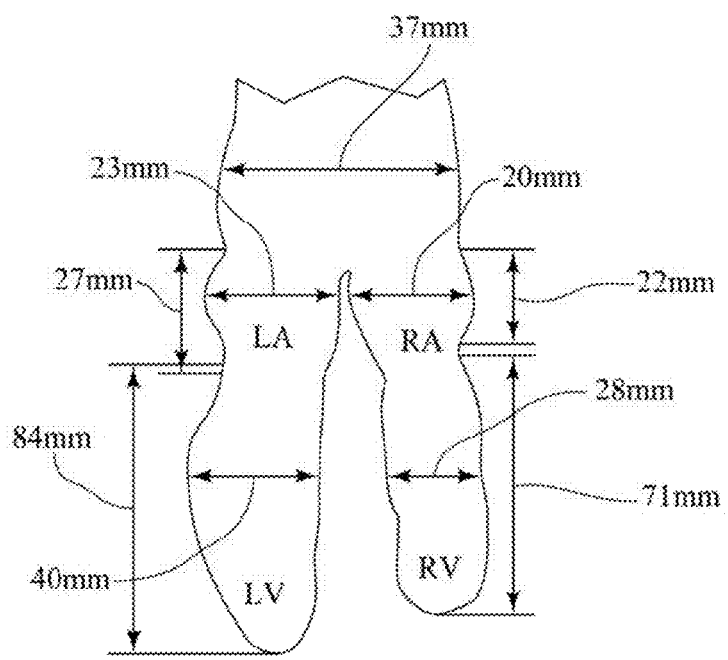
FIG. 5 depicts an internal five-segment insert that is placed in a mold to form the interior surfaces of the cardiac phantom of FIGS. 1-3.

Referring now to FIGS. 4 and 5 along with FIGS. 1-3, the multimodal phantom 10 can be produced using a mold, e.g. one with interior surfaces that mimic the exterior surfaces of a heart. The widest dimensions of a suitable mold are shown in FIG. 4.

A five-segment polymer clay mold insert, such as the one shown in FIG. 5, is inserted into the suitable cardiac phantom mold. For example, a suitable silicone-cardiac mold can be produced from a post-mortem sheep or human heart. Four segments of the mold insert simulate the heart's four chambers (e.g. 32, 34, 40, 42) and the fifth segment is used to make a connecting joint (i.e. upper portion 50) to attach the phantom to the connecting tube. Dimensions of the segments of the clay mold insert are identified in FIG. 5. The clay insert has exterior surfaces which mimic the interior wall surfaces of a heart, e.g. the left and right atriums and left and right ventricles. The thickest wall sizes for the left ventricle and the right ventricle of the cardiac phantom produced are 12 mm and 4 mm respectively. The diameters for the mitral (bicuspid) valve 60 (FIG. 2) and the tricuspid valve 62 (FIG. 2) are 17 mm and 16 mm respectively.

As previously noted, the cardiac phantom 10 is produced, in one advantageous embodiment, from polyvinyl alcohol (PVA). More specifically, in that embodiment, the cardiac phantom 10 is manufactured from a 10% starting material solution of PVA as the base material (i.e. 90% water/10% PVA). The PVA solution is then stirred and heated up to 90° C. until it becomes clear. The solution is subsequently placed in a closed space to decrease water evaporation since it will confound the desired mechanical properties. Heating is then continued until the powder is fully dissolved.

In some implementations of the manufacturing procedure, the foregoing process can vary from 0.5 to 3 hours depending on the PVA manufacturer. Highly hydrolyzed (>99.9%) products dissolve faster, while overheating the solution leads to faster dissolution of the powder but destructs the chemical structure of the molecules. Practically, it is preferred to discard the final superficial thick layer of the solution in order to decrease the inhomogeneity of the phantom texture. Subsequently, the solution is gradually cooled down from 80° C. to room temperature.

Next, ultrasound and MR markers are added to the solution. Plastic microspheres of size 1-2 min made of silicon are utilized as ultrasound markers. Very dense PVA-C particles of size 1-3 mm are used as MRI markers. Consequently, the solution is poured into the cardiac mold with 5-segmented insert and left for 12 hours to extract the bubbles. The manipulations are minimized after this process since any additional manipulation can cause air bubbles. It is then gradually exposed to a temperature of −20° C. until it freezes.

The mold and the solution are kept at this temperature for 24 hours. At that time the molecules in the PVA solution are cross-linked with each other to make a tougher material called PVA cryogel (PVA-C). More specifically, PVA monomers having the chemical formula $CH_2CHOH$ are cross-linked to create a polymer having the formula $(CH_2CHOH)_n$ having 1,3-diol linkages.

The five-segment mold (FIG. 5) detaches into five pieces in the low temperature and the solution leaks in between the segments and makes thin membranes forming bicuspid valve 62 and tricuspid valve 60. Finally, the mold and the frozen gel are gradually exposed to the room temperature to avoid any additional inhomogeneity in the chemical process of the cryogel. At this point, the normal heart phantom has passed one freeze-thaw cycle. The freeze-thaw cycles enhances the cross-linking between polymer chains and makes the polymer stiffer.

In additional to the cardiac phantom 10, different cardiac phantoms can also be produced to test and configure, and adjust cardiac imaging devices. For example, in some embodiments, a cardiac phantom can be produced which mimics a diseased heart, such as one which has diseased tissue, by introducing stiffened portions into the polymer which comprises the cardiac phantom. In some embodiments, the stiffened portions can be produced by repeating freeze-thaw cycles.

In some embodiments, a pathologic cardiac phantom with stiffened portions to mimic diseased tissue is produced having stiffer inclusions embedded in a normal cardiac phantom. The inclusions, which can be obtained from a stiff donor phantom heart, simulate different pathologic cardiac segments. In some embodiments, the stiff segments are separately placed in the apical and mid-ventricular cardiac regions of a suitable mold, and the degree of the stiffness of each segment is then determined by the number of freeze-thaw cycles. Since each freeze-thaw cycle decreases the elasticity of the heart, the inclusions are able to mimic a range of scarred myocardial tissues. Then, after placing the stiff segments in the mold, a PVA solution can be added to fill the rest of the space in the mold. After one freeze-thaw cycle, the abnormal heart consists of a background of normal texture with one freeze-thaw cycle plus infarct-mimicking inclusions having one more freeze-thaw cycle. The attenuation of the PVA and speed of sound of the material increase after each freeze-thaw cycle. Since the PVA-C properties are described in detail in the art, and are thus known to one skilled in the art, they are not disclosed here [2,3,4]. In some embodiments, however, the speed of sound in PVA is 1527, 1540, 1545, and 1550 m/s and ultrasound attenuation is 0.4, 0.52, 0.57, and 0.59 db/em for 1, 4, 7 and 10 freeze-thaw cycles. Additionally, T1/T2 is 980/820, 690/605, 540/500, and 520/480 ms for 1, 4, 7 and 10 freeze-thaw cycles [2,3,4].

Figure 6:
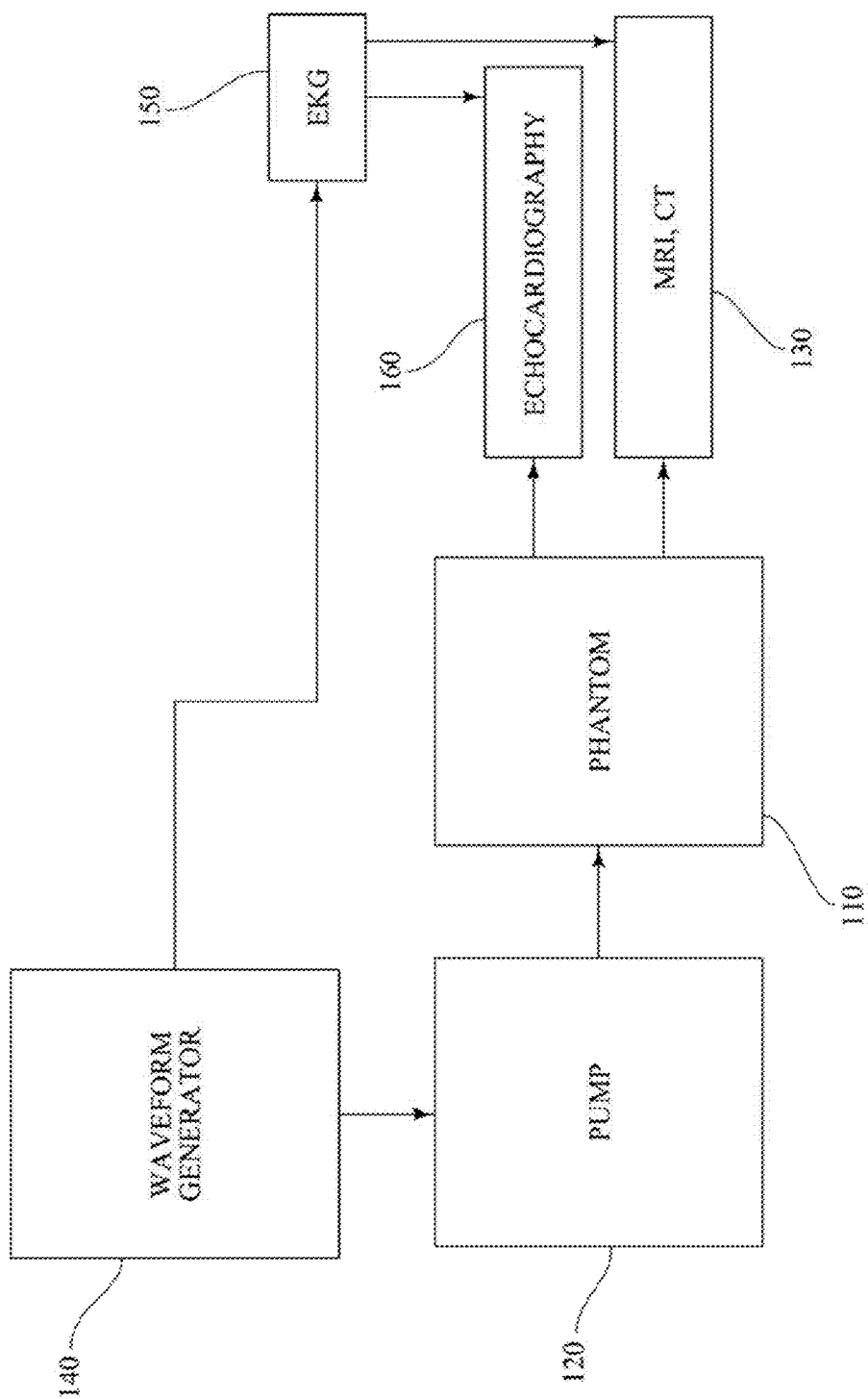
FIG. 6 depicts an apparatus for evaluating cardiac imaging devices using the cardiac phantom of FIGS. 1-3.
Figure 7:
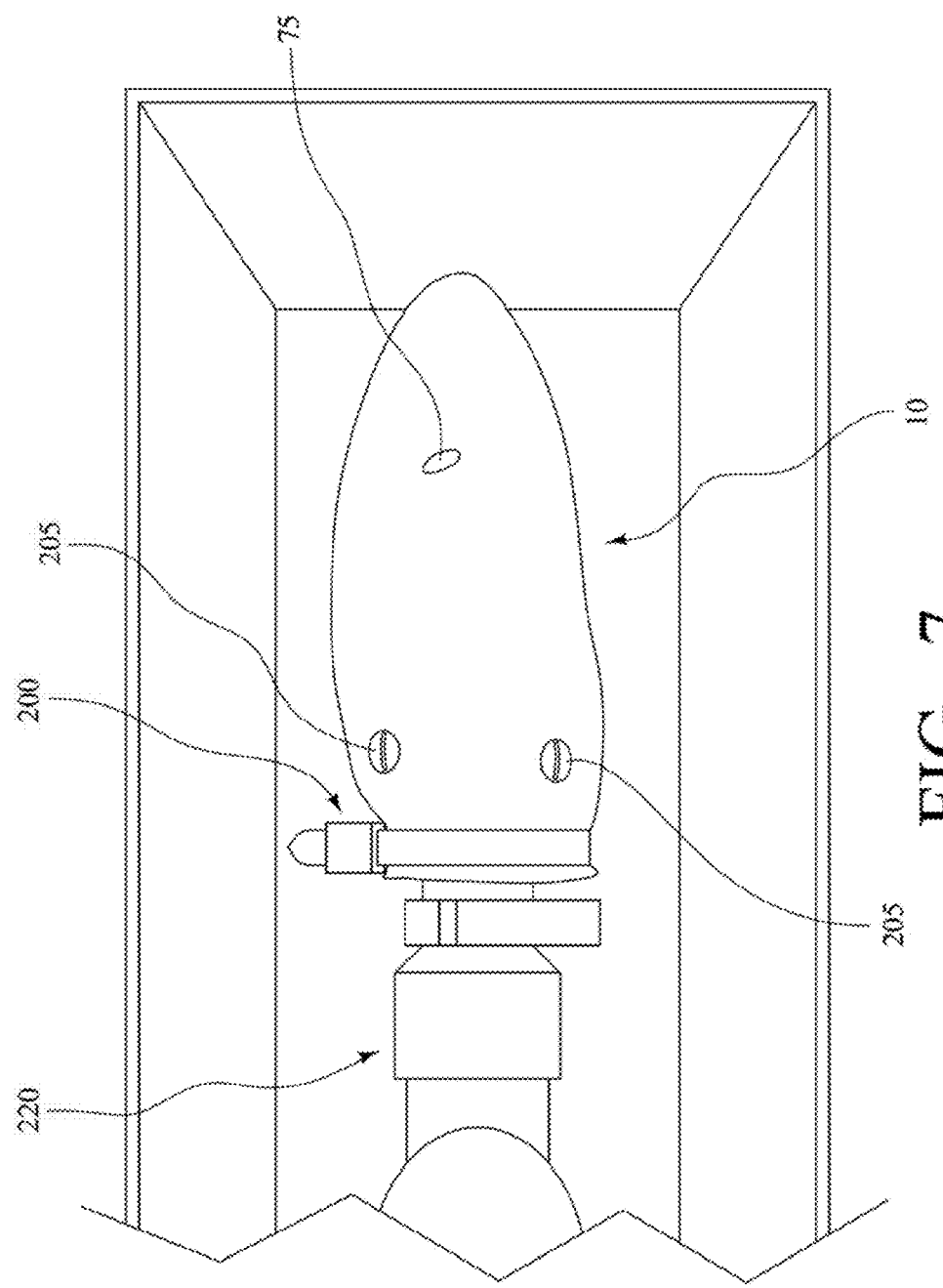
FIG. 7 depicts the cardiac phantom of FIGS. 1-3, sealed to a connector and placed inside a container, in accordance with the present invention.
Figure 8:
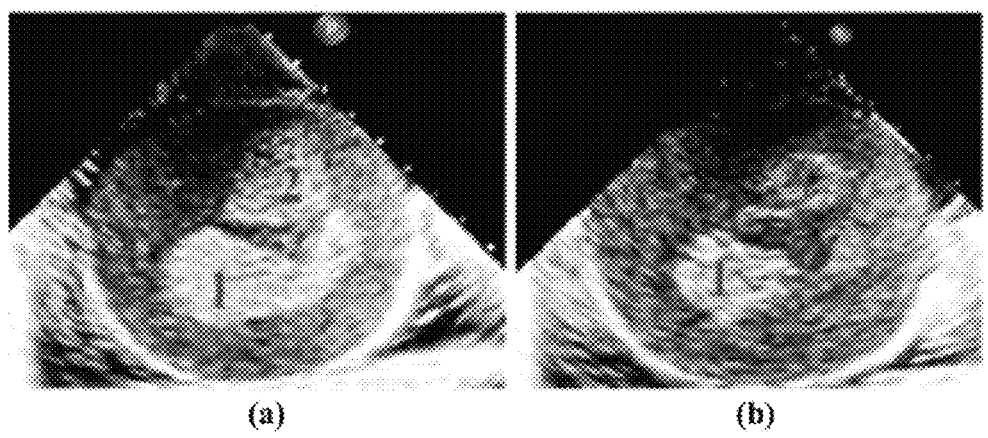
FIG. 8 comprises images of left panel (a) and right panel (b) where panel (a) is a short-axis echocardiography view in diastole and panel (b) is short-axis echocardiography view in systole (1: left ventricle (LV), 2: right ventricle (RV)).

Referring now to FIG. 6 along with FIGS. 1 and 2, the present cardiac phantoms 10, 110 can be used to simulate a heart's function. This can be accomplished by pumping a fluid through the cardiac phantoms 10, 110 or a pathologic cardiac phantom using pump 120. The simulation can be evaluated using an appropriate cardiac imaging apparatus 130. Referring now to FIG. 7 along with FIGS. 1, 2, and 6, to assemble the apparatus, the cardiac phantom 10, 110 is attached to a step-like connection of a connecting tube 220 using a large caliber plastic clamp 200 and three plastic screws 205 in order to keep the set-up free of ferromagnetic parts. The connection is designed as a wide and solid tube to decrease the additional resistance or nonlinear response of the fluid. A solution of 50% water and 50% glycerol was used to mimic the blood since glycerol is able to simulate blood viscosity and ultrasound scattering. Two different approaches can be considered to periodically contract and expand the cardiac phantom via a fluid waveform generator 140 such as: 1) Computer controlled fluid wave generation; and 2) Human controlled wave generation.

Computer controlled set up is more accurate and reproducible but requires more time and space for installation. In the first approach, the pump 120 is an MR-compatible pump (Shelley Medical Imaging Technologies, London, Ontario) connected to the phantom 10, 110 using a step-like connection. The pump is controlled by a computer placed outside the MR room. Different waveforms can be generated by the fluid pump to simulate a wide range of cardiac outputs and different types of cardiac pathologies. A trigger EKG 50 is generated by the central computer via EKG 150 to synchronize the MRI 130 and echocardiography 160 image acquisition. Human controlled wave generation is based on manual contraction and relaxation of a contractile bag attached to the connecting tube. Although this approach is not as reproducible as the computer controlled pump, the set up and transportation are easy and fast.

As shown in FIG. 7, in one exemplary embodiment, the cardiac phantom 10 and the connections were placed inside a plexiglass container covered with polypropylene pads covering the inside and outside surfaces. The propylene lining (pads) is able to match the acoustic impedance of the chamber with air and decrease back scattering from the plexiglass wall. The container can be fully closed to minimize the splashing of the fluid. Additional rulers, calipers and MR markers are used to calibrate the set up and measure the displacements if needed. The ultrasound transducer is fixed using a clamp with 5 degrees of freedom to cover all the imaging orientations. The displacements of the transducer can be measured by calipers. With the proposed experimental set-up, it is possible to acquire images from any direction including apical and short axis views.

Figure 9:
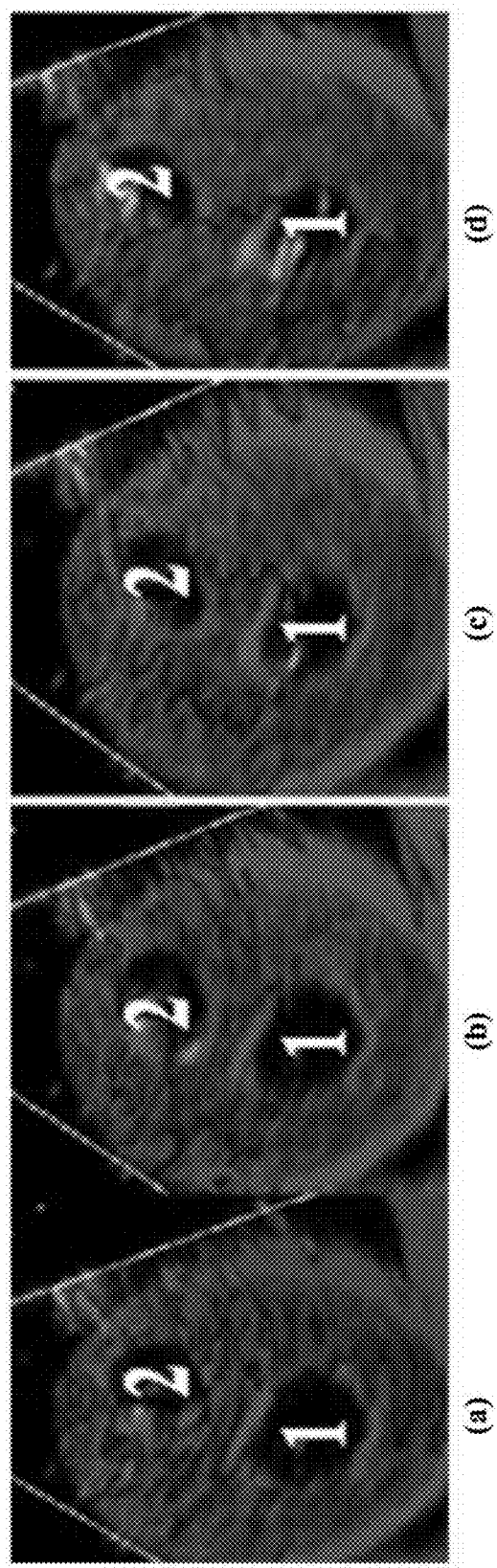
FIG. 9 depicts a series of images (a)-(d) of the cardiac phantom of FIGS. 1-3 using TDI imaging in the short-axis view in different phases of the cardiac cycle simulation (early systole to end diastole).
Figure 10:
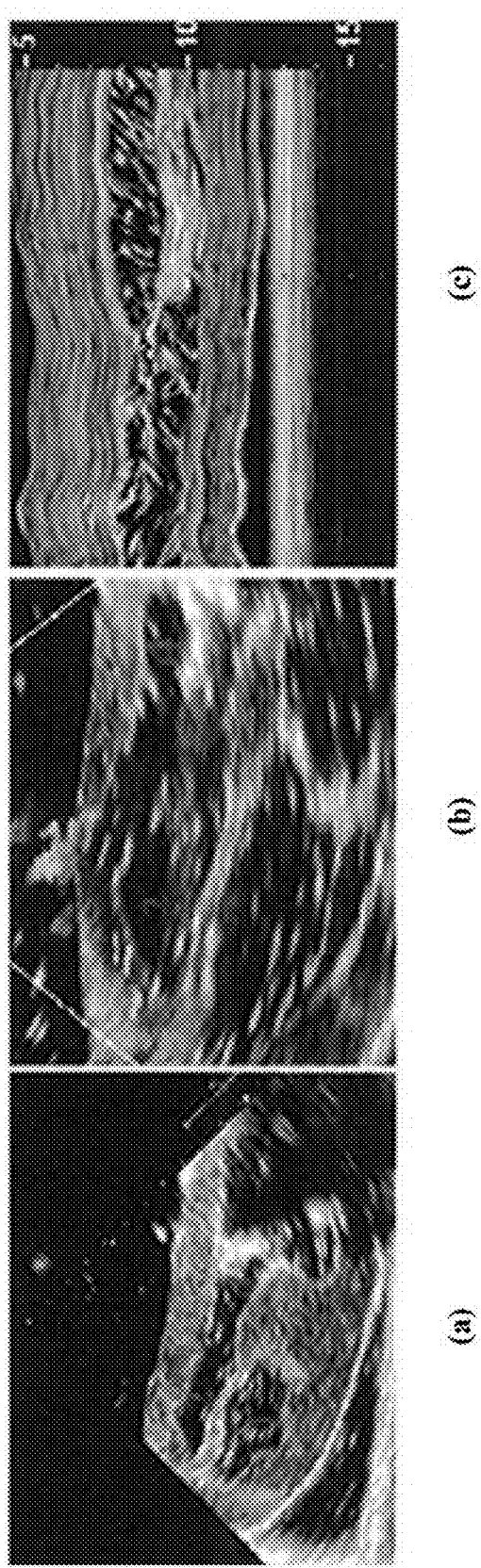
FIG. 10 comprises images (a)-(c) of the cardiac phantom of FIGS. 1-3, where panel (a) is a long-axis echocardiography view, panel (b) is a Doppler view of the tricuspid valve and RV outlet and panel (c) is an m-mode imaging of the same long-axis view (1: left ventricle (LV), 2: right ventricle (RV), 3: left atrium (LA), 4: right atrium (RA)).

FIG. 7 illustrates the inside of the phantom set up as well as the sealing clamps and connection pieces. Using the set up, image acquisition was performed using different echocardiographic views on a Philips iE33 workstation, transducer frequency 3 MHz. 2D, 3D and TDI images may be acquired and analyzed for evaluation studies from different orientations and views. Short axis B-mode, short-axis TDI and long-axis B-mode echo images are shown in FIG. 9, panels (a)-(d), respectively. Table 1 (below) shows the averaged regional analysis of the cardiac motion using TDI images. The range of the displacements is in accordance to the normal cardiac displacement range.

TABLE 1

Regional TDI motion (cm/s) of the mid ventricular segments in end-diastole, mid-diastole and end-systole.

|  | Mid antero-septal | Mid anterior | Mid antero-lateral | Mid infero-lateral | Mid inferior | Mid infero-septal |
|---|---|---|---|---|---|---|
| End-systole | 1.3 | 8.7 | 5.2 | 6.1 | 4.9 | 2.8 |
| mid-diastole | 5.9 | 7.6 | 9.7 | 5.7 | 1.6 | 0.7 |
| End-diastole | −4.7 | −3.4 | 2.0 | −3.1 | 0.2 | 0.4 |

Figure 11:
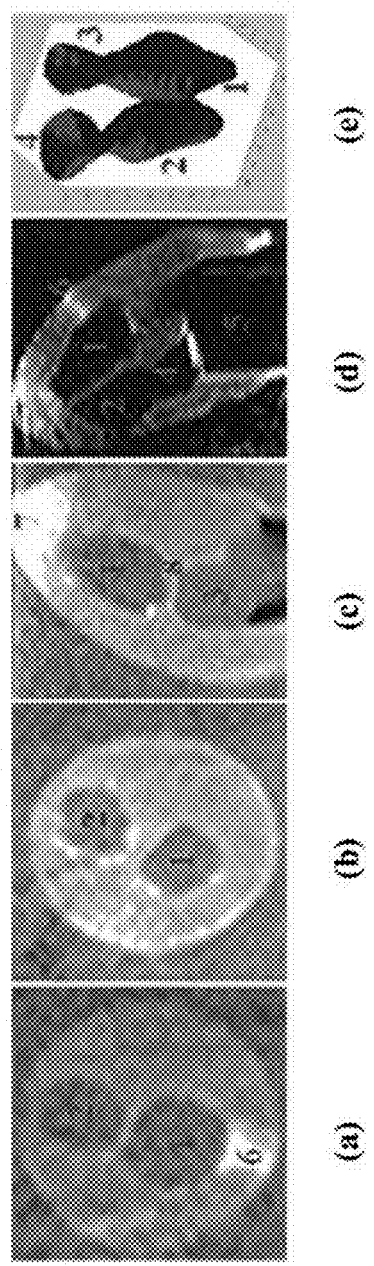
FIG. 11 comprises a series of images in which panel (a) is a static upper mid-ventricular MR slice of the phantom, panel (b) is a static MR slice in the lower "mid-ventricle" of the phantom, panel (c) is a long-axis MR view of the phantom, panel (d) is a coronal MR slice of the phantom, and panel (e) is a reconstruction of the endocardial contours of the phantom in 3D (1: LV, 2: RV, 3: LA, 4: RA, 5: connecting joint, 6: mid-ventricular inclusion obtained from a stiff donor heart, 7: apical inclusion obtained from a stiff donor heart, 8: Mitral valve).

The images of FIG. 11 show a further analysis of the cardiac phantom and were acquired using T1 weighted FFE, TE/TR 0.8/2.08 ms, FA 90°, slice thickness 6 mmm, spatial resolution 0.625×0.625-1.5 mm, 3D FOV 224×224×189 mm, and number of slices 24. Panel (d) (FIG. 11) was acquired using TE/TR 1.17/2.34 ms, FA 90°, slice thickness 6 mm, spatial resolution 1.70×1.70×1.5 mm, 3D FOV 224×224×189 mm, and number of slices 24. A 3D reconstruction of the four cavities based on manual delineation is shown in panel (e) (FIG. 11). The high signal regions in panels a, b, d (FIG. 11) illustrate the regions that simulate the scar.

Figure 12:
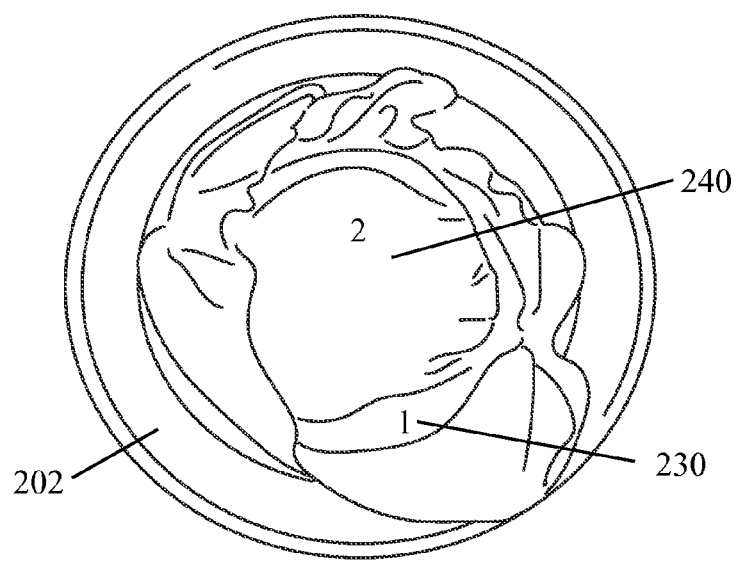
FIG. 12 is a top perspective view of an external silicone mold used to construct an alternative cardiac phantom in accordance with an additional embodiment of the present invention.
Figure 13:
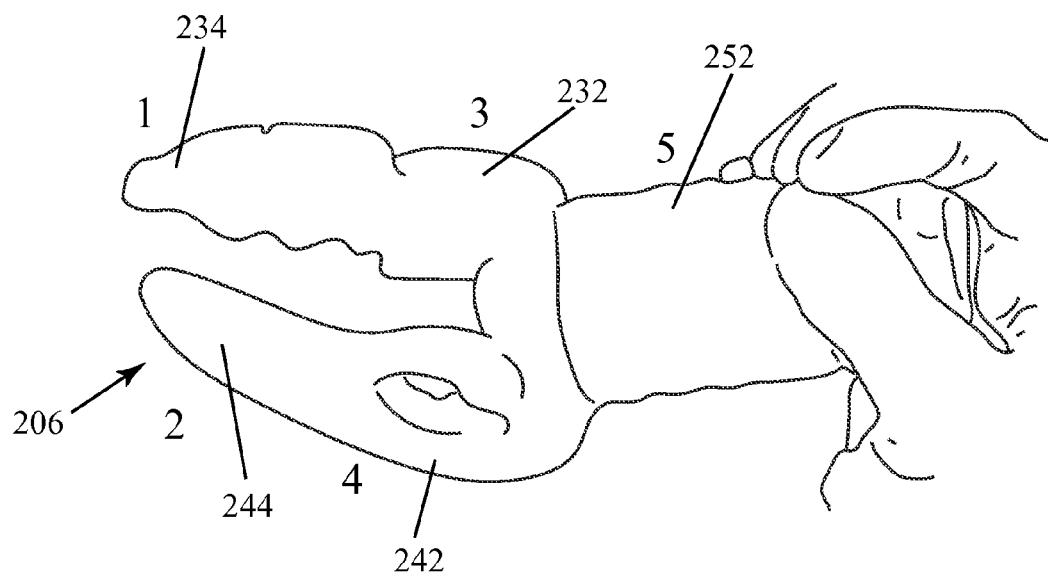
FIG. 13 is a side view of an internal cardiac mold (insert) used to construct an alternative cardiac phantom in accordance with the additional embodiment of the present invention.

Referring now to FIGS. 12-15, in one alternative embodiment, a cardiac phantom 210 (FIGS. 14-15) is constructed using a silicone-cardiac mold such as the external, mold 202 (FIG. 12) and an internal mold such as internal segment 206 (FIG. 13). For example, a post-mortem sheep heart can be used to construct mold 202 as a silicone cardiac mold.

In constructing the mold 202 with internal segment 206, the sheep heart is placed in a container, while the tip of the heart is placed at the bottom of the container and the base of the heart including the great vessels is positioned at the top of the container. The silicone solution is degassed and slowly poured in the container to fill the container. The solution is then left for an hour to harden (cure).

The final mold is composed of two parts: (1) an internal segment 206 that mimics the endocardial surface of the heart the ventricles and the atria (FIG. 13) and (2) an external segment, i.e. mold 202 that mimics the outer epicardial surface of the heart (FIG. 12). The mold 202 with internal segment 206 also provide a connection tube for the cardiac phantom 210. In some embodiments, transparent silicon facilitates observing the cardiac phantom construction process. FIG. 12 shows the external segments of the cardiac mold in which 230 refers to the location of the left ventricle and 240 refers to the location of the right ventricle. The mold 202 (shown in FIG. 12) is empty and with no PVA in order to illustrate the shape of the external surface of the heart. The internal segment 206 (mold insert) shown in FIG. 13 has a left ventricle segment 234, a right ventricle segment 244, a left atrium segment 232, a right atrium segment 242, and a connection segment 252.

Figure 14:
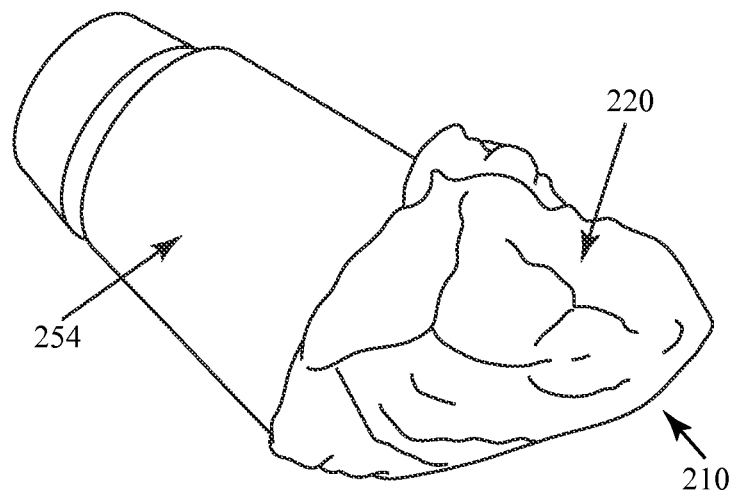
FIG. 14 is a side perspective view of the alternative cardiac phantom produced from the external cardiac mold of FIG. 12.
Figure 15:
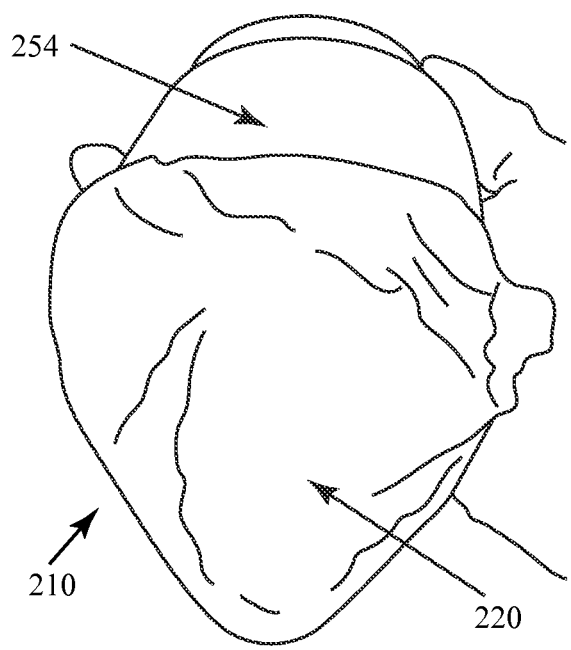
FIG. 15 is a bottom perspective view of the cardiac phantom of FIG. 14.

To manufacture the cardiac phantom 210, the internal segment 206 is typically fixed in the mold 202 of the phantom. Subsequently, PVA solution is poured into the mold 202 with the internal segment 206 in place to take on the shape of a heart in a manner similar to which the cardiac phantom 10 is constructed from PVA, PVA-C, ultrasound markers and MR markers, etc. as discussed above. Multiple freeze-thaw cycles can also be used to introduce higher stiffness, if desired, to mimic infarct cardiac tissue. The resulting cardiac phantom 210 has a main body portion 220 and connecting segment 254 (FIGS. 14 and 15).

Figure 16:
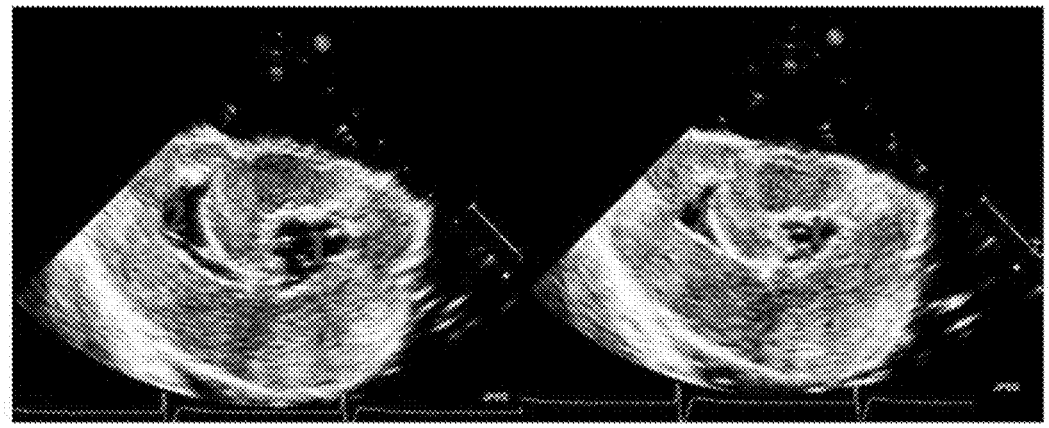
FIG. 16 comprises electrocardiograms in which, the left panel is a mid-ventricular short-axis echocardiography view in diastole, and the right panel is a short-axis echocardiography view in systole (wherein 1: left ventricle, 2: right ventricle).
Figure 17:
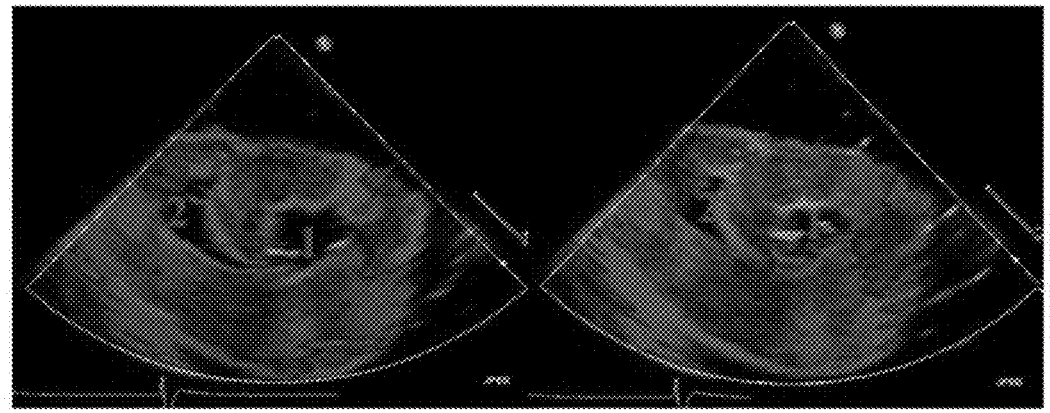
FIG. 17 comprises echocardiograms in which the left panel is a short-axis Tissue Doppler echocardiography view in diastole and the right panel is a short-axis Tissue Doppler echocardiography view in systole (wherein 1: left ventricle, 2: right ventricle), both at the same location as in FIG. 16.
Figure 18:
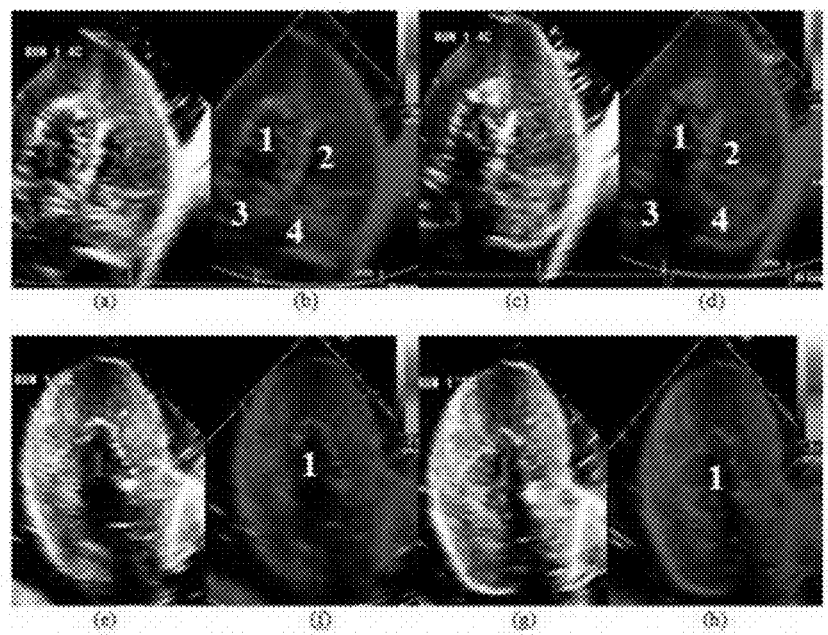
FIG. 18 comprises imaging panels (a)-(h) including four chamber B-mode and Tissue Doppler Imaging (TDI) views of the cardiac phantom of FIG. 14 in the medial-lateral plane in diastole (panels (a) and (b)) and systole (panels (c) and (d)), and long axis echocardiography B-mode and Tissue Doppler Imaging (TDI) views of the cardiac phantom in the medial-lateral plane in diastole (panels (e) (f)) and systole (panels (g) and (h)), where 1: LV, 2: RV, 3: LA, 4: RA).
Figure 19:
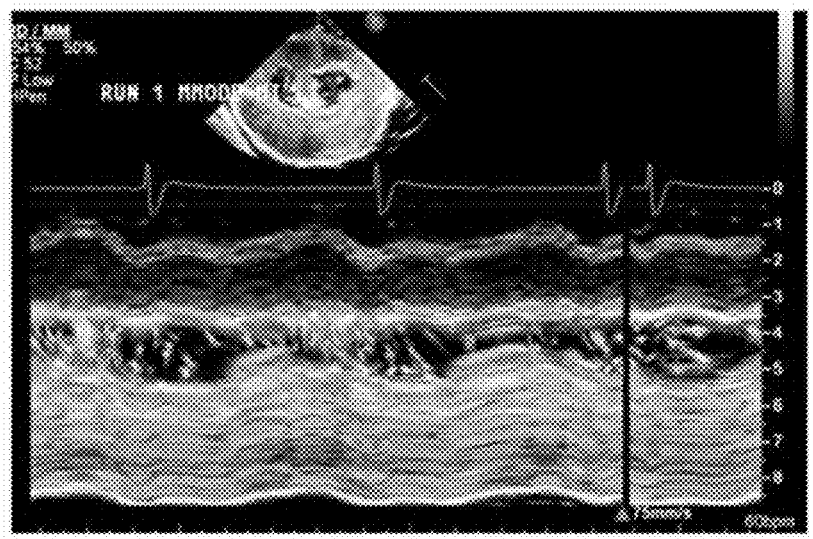
FIG. 19 is an m-mode imaging of the long-axis view of FIG. 18.
Figure 20:
FIG. 20 is a 3D volumetric imaging of the cardiac phantom of FIG. 14 on the Philips ie33 with a 3D probe.

The Cardiac phantom 210 can also be used in an apparatus for evaluating cardiac imaging devices, such as shown and discussed above with regard to FIGS. 6 and 7. In one implementation, image acquisition of the cardiac phantom 210 was performed using different echocardiographic views on a Philips iE33 workstation, transducer frequency 3 MHz 2D, 3D and TDI images were acquired and analyzed for evaluation studies from different orientations and views. Short axis B-mode, 73 short-axis TDI, long-axis and four chamber echo images are shown in FIGS. 16-18 respectively. FIG. 19 shows an M-mode image of the dynamic phantom, while FIG. 20 shows the full volume M-mode image of the phantom.

Figure 21:
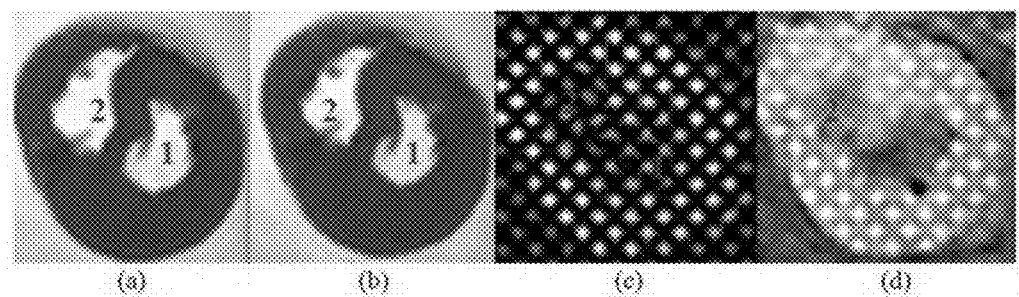
FIG. 21 comprises panels (a)-(d) which include a mid-ventricular Cine MR slice of the phantom in diastole (panel (a)) and systole (panel (b)), a midventricular tagged MR slice of the phantom imaged in diastole (panel (c)) and systole (panel (d)), where 1: LV, 2: RV.
Figure 22:
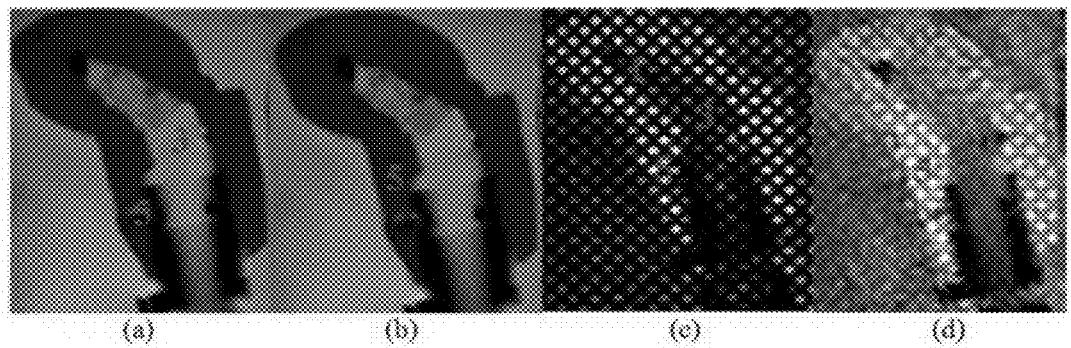
FIG. 22 comprises panels (a)-(d) in which panel (a) is a long axis Cine MR slice of the phantom in the medial-lateral plane in systole and panel (b) is a long axis Cine MR slice of the phantom in the medial-lateral plane in diastole, panel (c) is a tagged MR image of the same slice plane in systole and panel (d) is a tagged MR image of the same slice plane in diastole.
Figure 23:
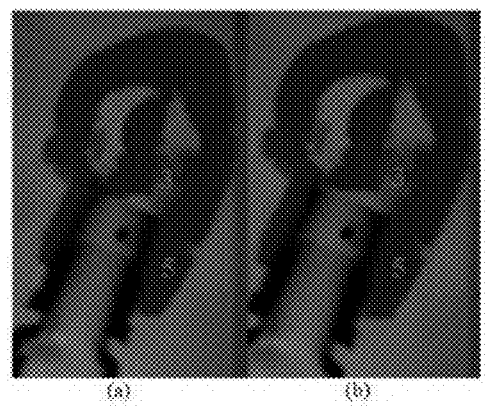
FIG. 23 comprises panels (a) and (b) in which panel (a) depicts a four-chamber Cine MRI of the cardiac phantom of FIG. 14 in the medial-lateral plane in systole and panel (b) depicts a four-chamber Cine MRI of the cardiac phantom of FIG. 14 in the medial-lateral plane in diastole (where 1: LV, 2: RV, 3: LA, 4: RA).
Figure 24:
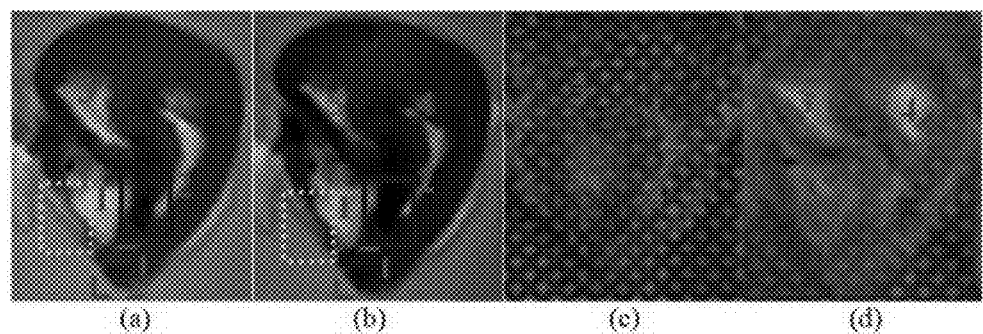
FIG. 24 comprises panels (a)-(d) in which panel (a) depicts a four chamber Cine MR image showing the pathologic features of the cardiac phantom of FIG. 14 in the medial-lateral plane in end-diastole and panel (b) depicts a four chamber Cine MR image showing the pathologic features of the cardiac phantom of FIG. 14 in the medial-lateral plane in end-systole, panel (c) is a tagged MRI image of the same slice in end-diastole and panel (d) is a tagged MRI image of the same slice in end-systole (d) (where 1: LV, 2: RV, 3: LA, 4: RA, solid rectangle: stiff inclusion in midantero-septal region, dashed shed rectangle: stiff inclusion placed at apex, dotted rectangle: aneurysm in the LV wall).

FIG. 21 illustrates Cine and tagged short axis MR views of the cardiac phantom 210. Cine MRI images were collected using a 1.5 T Philips Achieva scanner, T1 weighted FFE, TE/TR 2/3 ms, FA 60o, 11 phases for the R-R interval, and 3D FOV 256×256×189 mm. Cine tagged MR images were collected on the same scanner, TE/TR 2/4 ms, FA 15o, and 3D FOV 224×224×189 mm, slice thickness 8 mm, gap 1 mm, and 11 temporal phases. FIG. 22 shows Cine long axis, tagged long axis, and four chamber Cine MR images of the phantom. FIG. 23 shows the pathologic features of the phantom.

It will be understood that various details of the presently disclosed subject matter can be changed without departing from the scope of the subject matter disclosed herein. Furthermore, the foregoing description is for the purpose of illustration only, and not for the purpose of limitation.

REFERENCES

Throughout this document, various references are mentioned. All such references are incorporated herein by reference, including the references set forth in the following list:

1. Kasper D. L., Braunwald E., Fauci A. S., et al.: Harrison's Principles of Internal Medicine, McGraw-Hill Publishing, New York (2005)
2. Surrey, K. J. M., Austin, H. J. B., Fenster, A, Peters, T. M.: Poly (vinyl alcohol) cryogel phantoms for use in ultrasound and MR imaging. Phys Med Bioi., vol. 49, pp. 5529-5546 (2004).
3. Fromageau, J., Brusseau, E., Vray, D., Gimenez, G., and Delachartre, P.: Characterization of PYA cryogel for intravascular ultrasound elasticity imaging. IEEE Trans Ultrasonic Ferroelectric Freq Control, vol. 10, pp. 1318-1324 (2003)
4. K. C. Chu and B. K. Rutt, "Polyvinyl alcohol cryogel: An ideal phantom material for MR studies of arterial flow and elasticity. Magn Reson Med, vol. 37, pp. 314-319 (1997).
5. Martin, O., Culjat, D., Goldenberg, D., Tewari, P., Singh, R. S.: A Review of Tissue Substitutes for Ultrasound Imaging. Ultrasound in Medicine & Biology, Volume 36, Issue 6, 861-873 (2010).

The invention claimed is:

1. A multimodal cardiac phantom, comprising:
a body structure defining a first compartment and a second compartment, the first compartment and the second compartment each including a hollow upper chamber and a hollow lower chamber; said body structure having a shape to simulate a heart and comprised of a material configured to mimic elasticity, ultrasound, and magnetic properties of a cardiac tissue, a portion of the body structure comprised of a stiff polymeric material to thereby mimic diseased cardiac tissue.

2. The multimodal cardiac phantom of claim 1, wherein the body structure comprises cross-linked polyvinyl alcohol cryogel (PVA-C).

3. The multimodal cardiac phantom of claim 2, wherein the body structure further comprises dense PVA-C particles which function as MRI markers.

4. The multimodal cardiac phantom of claim 3, wherein the PVA-C particles have an average diameter of 1-3 mm.

5. The multimodal cardiac phantom of claim 2, wherein the body structure further comprises silicon microspheres which function as ultrasound markers.

6. The multimodal cardiac phantom of claim 1, further comprising an upper portion defining a connecting chamber for connecting the body structure to a connecting tube and for placing the first compartment and the second compartment in fluid communication with each other and with the connecting chamber.

7. The multimodal cardiac phantom of claim 1, further comprising a first valve separating the upper chamber of the first compartment from the lower chamber of the first compartment and a second valve separating the upper chamber of the second compartment from the lower chamber of the second compartment.

8. The multimodal cardiac phantom of claim 1, wherein the upper portion further defines one or more holes for securing the upper portion to a connecting tube.

9. An apparatus for simulating a cardiac structure and function, comprising:
a cardiac phantom, having:
a body structure defining a first compartment and a second compartment, the first compartment and the second compartment each including a hollow upper chamber and a hollow lower chamber; said body structure having a shape to simulate a heart and comprised of a material configured to mimic elasticity, ultrasound, and magnetic properties of a cardiac tissue, the body structure including an amount of a stiff PVA material having a shape and elasticity different than that of the material used for a remainder of the body structure such that the body structure is configured to mimic diseased cardiac tissue;
a pump for transferring an amount of fluid to the cardiac phantom;
a connecting tube for connecting the cardiac phantom to the pump; and
a waveform generator operably connected to the pump for controlling the timing and amount of fluid delivered to the cardiac phantom.

10. A method for evaluating a cardiac imaging system, comprising:
providing a cardiac phantom, having:
a body structure defining a first compartment and a second compartment, the first compartment and the second compartment each including a hollow upper chamber and a hollow lower chamber; said body structure having a shape to simulate a heart and comprised of a material configured to mimic elasticity, ultrasound, and magnetic properties of a cardiac tissue;
pumping an amount of fluid into the cardiac phantom;
imaging the body structure of the cardiac phantom as the fluid is being pumped; and
evaluating one or more images obtained from the imaging of the body structure of the cardiac phantom.

11. The method of claim 10, wherein the body structure comprises cross-linked polyvinyl alcohol cryogel (PVA-C).

12. The method of claim 11, wherein the body structure comprises dense PVA-C particles which function as MRI markers.

13. The method of claim 11, wherein the body structure comprises silicon microspheres which function as ultrasound markers.

14. A method for manufacturing a multimodal cardiac phantom, said method comprising:
heating a polymer to a temperature to liquefy the polymer;
introducing a liquefied polymer into a mold having a mold insert, the mold having internal surfaces which mimic the exterior shape of a heart and the mold insert having an exterior surface and shape which mimics the interior wall surfaces of the left atrium and left ventricle chambers and the right atrium and right ventricle chambers of a heart;
cooling the liquefied polymer to harden the polymer to form a multimodal cardiac phantom having a body structure defining a first compartment and a second compartment, the first compartment and the second compartment each including a hollow upper chamber and a hollow lower chamber; said body structure having a shape to simulate a heart and comprised of a material configured to mimic elasticity, ultrasound, and magnetic properties of a cardiac tissue;

removing the cardiac phantom from the mold, wherein the cardiac phantom comprises left and right upper chambers and left and right lower chambers produced from the mold insert; and introducing stiffened portions into the polymer which comprises cardiac phantom to thereby mimic diseased cardiac tissue.

15. The method of claim 14, wherein the polymer is polyvinyl alcohol.

16. The method of claim 14, further comprising adding dense PVA-C particles to the liquefied polymer.

17. The method of claim 14, further comprising adding silicon microspheres to the liquefied polymer.

18. The method of claim 14, further comprising freezing the liquefied polymer and cross-linking the polymer to produce polyvinyl alcohol cryogel (PVA-C).

19. The method of claim 14, wherein the mold insert has two channels which produce a first and second valve, respectively, in the cardiac phantom.

* * * * *